(12) United States Patent
Bergmann et al.

(10) Patent No.: US 7,157,081 B2
(45) Date of Patent: Jan. 2, 2007

(54) USES OF ALDOSE-1-EPIMERASE (MUTAROTASE) FOR DIAGNOSIS AND THERAPY OF INFLAMMATORY DISEASES AND SEPSIS

(75) Inventors: Andreas Bergmann, Berlin (DE); Joachim Struck, Berlin (DE); Monika Ühlein, Berlin (DE)

(73) Assignee: B.R.A.H.M.S Aktiengesellschaft, Hennigsdorf (DE)

( * ) Notice: Subject to any disclaimer, the term of this patent is extended or adjusted under 35 U.S.C. 154(b) by 0 days.

(21) Appl. No.: 10/497,683

(22) PCT Filed: Nov. 29, 2002

(86) PCT No.: PCT/EP02/13523

§ 371 (c)(1),
(2), (4) Date: Nov. 29, 2004

(87) PCT Pub. No.: WO03/048780

PCT Pub. Date: Jun. 12, 2003

(65) Prior Publication Data

US 2005/0130242 A1    Jun. 16, 2005

(30) Foreign Application Priority Data

Dec. 7, 2001    (EP)    ................... 01129121

(51) Int. Cl.
*A61K 38/43*    (2006.01)
(52) U.S. Cl. .................................................... 424/94.1
(58) Field of Classification Search ............. 424/94.1, 424/94.6, 94.61
See application file for complete search history.

(56) References Cited

U.S. PATENT DOCUMENTS 5,639,617 A    6/1997    Bohuon
6,756,483 B1 *  6/2004    Bergmann et al. .......... 530/399

FOREIGN PATENT DOCUMENTS

| DE | 198 47 690 A1 | 4/2000 |
| DE | 101 19 804 A1 | 10/2002 |
| DE | 101 30 985 A1 | 1/2003 |
| DE | 101 31 922 A1 | 1/2003 |
| WO | WO 00/22439 | 4/2000 |
| WO | WO02090521 A2 * | 11/2002 |

OTHER PUBLICATIONS

Naslund B. et al. Glucose determination in samples taken by microdialysis by peroxidase-catalyzed luminol chemiluminescence. Anal. Biochem. Jan. 1991; 192(1): 237-42.*
Meisner M. et al. "Comparision of procalcitonin (PCT) and C-reactive protein (CRP) plasma concentrations at different SOFA scores during the course of sepsis and MODS", Crit. Care 1999, 3: 45-50, entire document.*
Menzel C. et al, "Development of biosensors based . . . process monitoring. part I. Development of the biosensors and their characterization", Analytica Chimica Acta, 1995, 317: 259-264. entire document.*
A. Beishuizen et al., "Endogenous Mediators in Sepsis and Septic Shock", *Advances in Clinical Chemistry*, vol. 33 (1999) 55-131.
C. Gabay et al., "Acute Phase Proteins and Other Systemic Responses to Inflammation", *The New England Journal of Medicine*, vol. 340, No. 6, (1999) 448-454.
K. Reinhart et al., "Sepsis and septischer Schock" [Sepsis and septic shock], in: *Intensivmedizin*, Georg Thieme Verlag, Stuttgart (2001) 756-760.
M. Assicot et al., "High serum proclacitonin concentrations in patients with sepsis and infection", *The Lancet*, vol. 341, No. 8844 (1993) 515-518.
W. Karzai et al., "Procalcitonin—A New Indicator of the Systemic Response to Severe Infection", *Infection*, vol. 25 (1997) 329-334.
M. Oczenski et al., "Procalcitonin: a new parameter for the diagnosis of bacterial infection in the peri-operative period", *European Journal of Anaesthesiology* vol. 15 (1998) 202-209.
H. Redl et al., "Procalcitonin release patterns in a baboon model of trauma and sepsis: Relationship to cytokines and neopterin" *Crit Care Med* vol. 28, No. 11 (2000) 3659-3663.
H. Redl et al., "Non-Human Primate Models of Sepsis" *Sepsis*, vol. 2 (1998) 243-253.
E.A. Panacek, "Anti-TNF strategies" *Journal für Anästhesie und Intensivbehandlung*, No. 2 (2001) 4-5.
T. Calandra et al., "Protection from septic shock by neutralization of macrophage migration inhibitory factor" *Nature Medicine*, vol. 6, No. 2 (2000) 164-170.
Ghillani et al., "Monoclonal antipeptide antibodies as tools to dissect closely related gene products" *The Journal of Immunology*, vol. 141, No. 9 (1988) 3156-3163.
Ghillani et al., "Identification and Measurement of Calcitonin Precursors in Serum of Patients with Malignant Diseases" *Cancer Research*, vol. 49, No. 23 (1989) 6845-6851.
J. Klose, "Fractionated Extraction of Total Tissue Proteins from Mouse and Human for 2-D electrophoresis" *Methods in Molecular Biology*, vol. 112: 2-D Proteome Analysis Protocols, Humana Press Inc., Totowa, NJ.
J. Klose et al., "Two-dimensional electrophoresis of proteins: An updated protocol and implications for a functional analysis of the genome" *Electrophoresis* 16 (1995) 1034-1059.

(Continued)

*Primary Examiner*—Sandra E. Saucier
*Assistant Examiner*—Satyendra K. Singh
(74) *Attorney, Agent, or Firm*—Mayer Brown Rowe & Maw; Paul L. Sharer (57) ABSTRACT

Uses of aldose 1-epimerase (SEQ ID NO:3) from body fluids or body tissues in human and veterinary medicine as a marker peptide for diagnosis, for prognosis of the course and for monitoring of the course of inflammations and infections and/or as a target for therapeutically influencing the course of inflammations and/or infections.

8 Claims, 4 Drawing Sheets

OTHER PUBLICATIONS

V. Neuhoff et al., "Improved staining of proteins in polyacrylamide gels including isoelectric focusing gels with clear background at nanogram sensitivity using Coomassie Brilliant Blue G-250 and R-250" *Electrophoresis* 9 (1988) 255-262.

A. Otto et al., "Identification of human myocardial proteins separated by two-dimensional electrophoresis using an effective sample preparation for mass spectrometry", *Electrophoresis* 17 (1996) 1643-1650.

G. Neubauer et al., "Mass spectrometry and EST-database searching allows characterization of the multi-protein spliceosome complex" *Nature Genetics*, vol. 20 (1998) 46-50.

J. Lingner et al., "Reverse Transcriptase Motifs in the Catalytic Subunit of Telomerase", *Science*, vol. 276 (1997) 561-567.

M. Mann et al., "Use of mass spectrometry-derived data to annotate nucleotide and protein sequence databases" TRENDS in Biochemical Sciences, vol. 26, No. 1 (2001) 54-61.

Weibel "A Coupled Enzyme Assay for Aldose-1-epimerase EC-5.1.3.3" *Analytical Biochemistry* 70:2 (1976) 489-494.

Strausberg "Hypothetical 37,8 kDA Protein" EMBL Database, Database Accession No. Q96C23 (Dec. 2001).

\* cited by examiner

USES OF ALDOSE-1-EPIMERASE (MUTAROTASE) FOR DIAGNOSIS AND THERAPY OF INFLAMMATORY DISEASES AND SEPSIS

CROSS REFERENCE TO RELATED APPLICATION

This application is the National Phase application of International Application No. PCT/EP02/13523, filed Nov. 29, 2002, which designates the United States. This application, in its entirety, is incorporated herein by reference.

The present invention relates to novel uses of the enzyme aldose 1-epimerase (also known as mutarotase; frequently abbreviated below to "A1E" or simply "epimerase") for the medical diagnosis and therapy of inflammatory diseases and sepsis. It is based on the detection for the first time of greatly increased concentrations of aldose 1-epimerase in liver tissue of primates in which a sepsis or systemic inflammation had been produced experimentally by toxin administration.

The present invention has its origin in intensive research work by the Applicant in relation to further improvements of the diagnosis and therapy of inflammations and infections, in particular of inflammations of infectious aetiology and sepsis.

Inflammations are defined very generally as certain physiologically reactions of an organism to different types of external effects, such as, for example, injuries, burns, allergens, infections by microorganisms, such as bacteria and fungi and viruses, to foreign tissues which trigger rejection reactions, or to certain inflammatory endogenous conditions of the body, for example in autoimmune diseases and cancer. Inflammations may occur as harmless, localized reactions of the body but are also typical features of numerous serious chronic and acute diseases of individual tissues, organs, organ parts and tissue parts.

Local inflammations are generally part of the healthy immune reaction of the body to harmful effects and hence part of the life-preserving defence mechanism of the body. If, however, inflammations are part of a misdirected reaction of the body to certain endogenous processes, such as, for example, in autoimmune diseases, and/or are of a chronic nature, or if they achieve a systematic extent, as in the case of systemic inflammatory response syndrome (SIRS) or in the case of a severe sepsis caused by infection, the physiological processes typical of inflammatory reactions go out of control and become the actual, frequently life-threatening pathological process.

It is now known that the origin and the course of inflammatory processes are controlled by a considerable number of substances which are predominantly of a protein or peptide nature or are accompanied by the occurrence of certain biomolecules for a more or less limited time. The endogenous substances involved in inflammatory reactions include in particular those which may be counted among the cytokines, mediators, vasoactive substances, acute phase proteins and/or hormonal regulators. The inflammatory reaction is a complex physiological reaction in which both the endogenous substances activating the inflammatory process (e.g. TNF-α) and deactivating substances (e.g. interleukin-10) are involved.

In systemic inflammations, as in the case of a sepsis or of septic shock, the inflammation-specific reaction cascades spread in an uncontrolled manner over the whole body and become life-threatening in the context of an excessive immune response. Regarding the current knowledge about the occurrence and possible role of individual groups of endogenous inflammation-specific substances, reference is made, for example, to A. Beishuizen et al., "Endogenous Mediators in Sepsis and Septic Shock", Advances in Clinical Chemistry, Vol. 33, 1999, 55–131; and C. Gabay et al., "Acute Phase Proteins and Other Systemic Responses to Inflammation", The New England Journal of Medicine, Vol.340, No. 6, 1999, 448–454. Since the understanding of sepsis and related systemic inflammatory diseases, and hence also the recognized definitions, have changed in recent years, reference is also made to K. Reinhart et al., "Sepsis and septischer Schock" [Sepsis and septic shock], in: Intensivmedizin, Georg Thieme Verlag, Stuttgart, N. Y., 2001, 756–760, where a modern definition of sepsis is given. In the context of the present Application, the terms sepsis and inflammatory diseases used are based on the definitions given in the stated three references.

Whereas at least in Europe the systemic bacterial infection detectable by a positive blood culture long characterized the term sepsis, sepsis is now primarily understood as being systemic inflammation which is caused by infection but, as a pathological process, has great similarities to systemic inflammations which are triggered by other causes. Said transformation in the understanding of sepsis has resulted in changes in diagnostic approaches. Thus, the direct detection of bacterial pathogens was replaced or supplemented by complex monitoring of physiological parameters and, more recently, in particular by the detection of certain endogenous substances involved in the sepsis process or in the inflammatory process, i.e. specific "biomarkers".

Of the large number of mediators and acute phase proteins which are known to be involved in an inflammatory process, the ones which are suitable for diagnostic purposes are in particular those whose occurrence is very specific for inflammatory diseases or certain phases of inflammatory diseases and whose concentrations change in a dramatic and diagnostically significant manner and which moreover have the stabilities required for routine determinations and reach high concentration values. For diagnostic purposes, the reliable correlation of pathological process (inflammation, sepsis) with the respective biomarker is of primary importance, without there being any need to know its role in the complex cascade of the endogenous substances involved in the inflammatory process.

Such an endogenous substance particularly suitable as a sepsis biomarker is procalcitonin. Procalcitonin is a prohormone whose serum concentrations reach very high values under the conditions of a systemic inflammation of infectious aetiology (sepsis), whereas it is virtually undetectable in healthy persons. High values of procalcitonin are also reached in a relatively early stage of a sepsis so that the determination of procalcitonin is also suitable for early diagnosis of a sepsis and for early distinguishing of a sepsis caused by infection from severe inflammations which have other causes. The determination of procalcitonin as a sepsis marker is the subject of the publication by M. Assicot et al., "High serum procalcitonin concentrations in patients with sepsis and infection", The Lancet, Vol. 341, No. 8844, 1993, 515–518; and the patents DE 42 27 454 C2 and EP 0 656 121 B1 and U.S. Pat. No. 5,639,617. Reference is hereby made to said patents and to early literature references mentioned in said publication for supplementing the present description. In recent years, the number of publications on the subject of procalcitonin has greatly increased. Reference is therefore also made to W. Karzai et al., "Procalcitonin—A New Indicator of the Systemic Response to Severe Infection", Infection, Vol. 25, 1997, 329–334; and M. Oczenski et al., "Procalcitonin: a new parameter for the diagnosis of bacterial infection in the peri-operative period", European Journal of Anaesthesiology 1998, 15, 202–209; and furthermore H. Redl et al., "Procalcitonin release patterns in a baboon model of trauma and sepsis: Relationship to cytokines and neopterin", Crit Care Med 2000, Vol. 28, No. 11, 3659–3663; and H. Redl et al., "Non-Human Primate Models of Sepsis", in: Sepsis 1998;2:243–253; and the further literature references cited therein, as typical of recent published reviews.

The availability of the sepsis marker procalcitonin has given considerable impetus to sepsis research, and intensive efforts are now being made to find further biomarkers which can supplement the procalcitonin determination and/or are capable of providing additional information for purposes of fine diagnosis or differential diagnosis. The search for potential new sepsis biomarkers is, however, complicated by the fact that frequently very little or nothing is known about the exact function or about the exact reasons for the occurrence of certain endogenous substances which are involved in inflammatory or septic processes.

The results of the experimental testing of a fruitful purely hypothetical approach to the determination of further potential sepsis markers are to be found in DE 198 47 690 A1 and WO 00/22439. There, it is shown that, in the case of sepsis, not only is the concentration of the prohormone procalcitonin increased but also significantly increased concentrations can be observed for other substances which may be included among the peptide prohormones. While the phenomenon described is well documented, the causes of the increase in the concentrations of prohormones in sepsis are still substantially unexplained.

In the present Application, a result of another fruitful, purely experimental approach in the search for further inflammation- or sepsis-specific biomolecules is reported. These experimental investigations, too, originate in the determination of procalcitonin in relation to systemic inflammatory reactions of infectious aetiology. Thus, it had been observed at a very early stage that the procalcitonin is evidently not formed in the same manner in sepsis as when it is a precursor for the hormone calcitonin. Thus, high procalcitonin levels were also observed in patients whose thyroid had been removed. The thyroid therefore cannot be the organ in which procalcitonin is formed or secreted during sepsis. In the publications by H. Redl et al., "Procalcitonin release patterns in a baboon model of trauma and sepsis: Relationship to cytokines and neopterin", Crit Care Med 2000, Vol. 28, No. 11, 3659–3663; and H. Redl et al., "Non-Human Primate Models of Sepsis", Sepsis 1998; 2:243–253, the results of experimental investigations which are said to be intended for explaining the formation of procalcitonin in sepsis are reported. In said work, an artificial sepsis is produced by endotoxin administration to primates (baboons), and the experimentally produced states in which the highest procalcitonin concentrations in the blood are reached are determined. A further development of the experimental animal model described in said work serves, in the context of the present Application, for determining novel endogenous sepsis-specific biomarkers of a peptic or protein nature, the occurrence of which is characteristic for sepsis or certain forms of sepsis and which therefore permit a specific diagnosis of sepsis. The primate model was chosen because of the very great similarity of the physiology of primates and humans and the high cross-reactivity with many therapeutic and diagnostic human reagents.

Since the endogenous substances formed during inflammations are part of the complex reaction cascade of the body, not only are such substances also of diagnostic interest but attempts are currently also being made, with considerable effort, to intervene therapeutically in the inflammatory process by influencing the formation and/or the concentration of individual substances of this type, in order to stop as early as possible the systemic spread of the inflammation, which spread is observed, for example, during sepsis. In this context, endogenous substances which have been shown to be involved in the inflammatory process are also to be regarded as potential therapeutic targets. Attempts based on certain mediators of the inflammatory process and intended to have a positive therapeutic influence on said process are described, for example, in E. A. Panacek, "Anti-TNF strategies", Journal für Anästhesie und Intensivbehandlung; No. 2, 2001, 4–5; T. Calandra et al., "Protection from septic shock by neutralization of macrophage migration inhibitory factor", Nature Medicine, Vol. 6, No. 2, 2000, 164–170; or K. Garber, "Protein C may be sepsis solution", Nature Biotechnology, Vol. 18, 2000, 917–918. These therapeutic approaches are intended to lower the concentrations of inflammation-promoting substances or to inhibit the formation of such substances, and to do so in particular with the use of specific antibodies (against TNF-α or MIF; cf. E.A. Panacek, "Anti-TNF strategies", Journal für Anästhesie und Intensivbehandlung; No. 2, 2001, 4–5; T. Calandra et al., "Protection from septic shock by neutralization of macrophage migration inhibitory factor", Nature Medicine, Vol. 6, No. 2, 2000, 164–170) or to increase the concentration of endogenous substances which have an inhibitory effect in the inflammation cascade (Protein C; K. Garber, "Protein C may be sepsis solution", Nature Biotechnology, Vol. 18, 2000, 917–918). The last-mentioned publication gives an overview of such attempts to have a therapeutic influence on the inflammatory process by influencing selected endogenous target molecules, which attempts have unfortunately generally met with little success to date. In view of the rather disappointing therapeutic approaches to date, there is great interest in identifying further endogenous biomolecules which are as inflammation- or sepsis-specific as possible and which, as therapeutic targets, also open up new prospects for success in fighting inflammation.

The present invention is based on the fact that the enzyme aldose 1-epimerase (mutarotase) is detectable in considerable concentrations in inflammations caused by infection in primates and humans, in contrast to healthy persons, in whom it is not found or is found only in concentrations at the analytical limit of detection, making said epimerase suitable both for diagnosis of inflammation/diagnosis of sepsis and as a novel therapeutic target.

The uses in diagnosis and therapy, which arise because of the occurrence of aldose 1-epimerase, detected for the first time, in the experimental simulation of inflammations or sepsis, are claimed in general form in Claim 1.

Claims 2 to 9 relate to diagnostic uses or methods.

Claim 10 relates in general form to the novel potential therapeutic uses, in particular in the area of the therapy of inflammations and infections, including sepsis, and Claims 11 to 14 relate to therapeutic applications of certain pharmaceutical compositions, which applications have the aim of influencing the physiological A1E concentrations or A1E enzyme effect.

As will be explained in more detail below in the experimental section, the invention is based on the fact that, after experimental triggering of an artificial sepsis in baboons by endotoxin administration (LPS from *Salmonella Typhimurium*) and working-up of liver tissue of the treated animals by 2D gel electrophoresis, a peptide or protein product identifiable only in the treated animals was found. This specific product was isolated from the electrophoresis gel, trypsin-digested and investigated by mass spectrometry. It proved to be aldose 1-epimerase (baboon) on the basis of the identification of two selected peaks which were more precisely characterized by tandem mass spectrometry and could be assigned to a hypothetical protein to be found in a human cDNA database, and the subsequent identification of this protein by comparison with the data for a human aldose 1-epimerase fragment or for aldose 1-epimerase from pigs.

On the basis of the identity of the sequences identified by mass spectrometry with partial sequences of the sequence data for aldose 1-epimerase which is to be found in databases, the identification of the human equivalent to the isolated protein spot as aldose 1-epimerase is to be regarded as unambiguous according to recognized criteria.

When, in the present Application, the peptide intended for diagnostic purposes or proposed for therapeutic purposes is referred to as "epimerase", this does not mean that such an epimerase must be 100% identical to the sequence according to SEQ ID NO:3. Rather, in the present Application, epimerase is defined as a peptide which, in the physiologically occurring form, has partial peptide sequences according to SEQ ID NO:1 (FGELPS) and SEQ ID NO:2 (PDGEEGY), and has high homology, i.e. preferably of more than 60%, more preferably 80%, to the sequence of the human epimerase according to SEQ ID NO:3.

The term epimerase also covers partial peptides of a peptide as defined above, which partial peptides can be used in particular in the preparation of reagents, for example selective antibodies, for the epimerase determination or preparation of assays for the epimerase determination in biological samples. Those sequences which are obtained after deletion of one or more amino acids or short peptide sequences from the peptide according to SEQ ID NO:3 are also to be regarded as epimerase or partial sequences thereof. Furthermore, partial sequences (fragments) suitable for diagnostic and/or therapeutic purposes are in particular those which comprise a sequence of at least three amino acids, preferably at least 6 amino acids, of the peptide SEQ ID NO:3.

For particular diagnostic or therapeutic purposes, the epimerase peptides according to the invention may also be animal peptides, in particular mammalian peptides, which should have at least 60% homology to the peptide with SEQ ID NO:3 and, for example, can be used for diagnostic purposes or in veterinary medicine.

The identification of the protein found only after triggering of sepsis or of inflammation in baboon liver tissue as aldose 1-epimerase (mutarotase; A1E; EC 5.1.3.3.) is of considerable scientific, diagnostic and therapeutic interest, said identification being regarded as unambiguous according to recognized criteria. Epimerase has long been known for enzymatic tissue activity. An identification of the human cDNA sequence, determined in the database, as a sequence coding for the complete human aldose 1-epimerase has to the best of our knowledge not yet been carried out. The epimerase activity has to date been the subject of investigations with a primarily scientific objective. Publications by Michael K. Weibel in: Analytical Biochemistry 70, 489–494 (1976), or Jane A. Beebe et al., in: Biochemistry 1998, 37, 14989–14997 (on galactose mutarotase), and the publications mentioned therein, may be mentioned here by way of example. In said papers, epimerases are discussed primarily as enzymes which catalyze the mutual conversion of α- and β-anomers of aldoses and which are assumed to be involved in sugar transport, e.g. in the kidney and intestine, and in sugar metabolism. For medical diagnosis and therapy, aldose 1-epimerase has played no role to date.

The present invention on the one hand provides protection, according to claim 1, for the uses stated therein of a peptide which is referred to as epimerase and, according to the above-mentioned definition, is defined primarily by the presence of the partial sequences of 6 or 7 amino acids according to SEQ ID NO:1 and SEQ ID NO:2, respectively, without there being any intention to impose restrictions with regard to the length and nature of further amino acid sequences. Human A1E is distinguishable from all other human peptides and proteins which are known and/or documented in databases by the presence of said two partial sequences. In the complete human form, human aldose 1-epimerase has the sequence according to SEQ ID NO:3.

On the basis of sequence SEQ ID NO:3 now known and the physiological role of human epimerase in combination with the findings on its increased formation in inflammations and sepsis, the human epimerase or fragments thereof can be synthesized or prepared by genetic engineering as recombination products for diagnostic and/or therapeutic purposes by methods which are now part of the prior art.

Furthermore, the epimerase peptides can be used by known methods of the modern prior art also for producing specific polyclonal and in particular monoclonal antibodies which are suitable as auxiliaries for the diagnostic determination of the peptides according to the invention and/or also as potential therapeutic agents. The production of suitable monoclonal antibodies against known partial peptide sequences is now part of the general prior art.

In the medical diagnostic determination of epimerase according to SEQ ID NO:3 or of selected partial peptides thereof, it is in principle possible to proceed as described, for example, for the selective procalcitonin determination in P. P. Ghillani et al., "Monoclonal antipeptide antibodies as tools to dissect closely related gene products", The Journal of Immunology, Vol. 141, No. 9, 1988, 3156–3163; and P. P. Ghillani et al., "Identification and Measurement of Calcitonin Precursors in Serum of Patients with Malignant Diseases", Cancer Research, Vol. 49, No. 23, 1989, 6845–6851; reference also being made expressly and additionally to the immunization techniques described there, which represent a possibility for obtaining monoclonal antibodies also against partial sequences of epimerase. Variations of the techniques described and/or further immunization techniques can be found by a person skilled in the art in relevant standard works and publications and can be applied in context.

The production of epimerase antibodies using techniques of direct genetic immunization with DNA should furthermore be mentioned expressly. It is furthermore within the scope of the present invention to use, for example, a cDNA of the desired epimerase or its partial peptides for the immunization, since it has been found in the past that the spectrum of the obtainable antibodies can be extended by such immunization techniques. Epimerase according to SEQ ID NO:3 or partial peptides thereof, for example those which contain the partial sequence SEQ ID NO:1, SEQ ID NO:2 and/or other partial sequences, can, on the basis of the available results, serve as specific marker peptides (biomarkers) for the diagnostic detection and for monitoring the course of inflammations and infections (in particular also of systemic infections of the sepsis type). As in the case of the determination of procalcitonin, the determination of epimerase can be effected by using a method for the differential early diagnosis or for the detection and for the assessment of the severity and for the therapy-accompanying assessment of the course of sepsis and infections, in such a method, the content of epimerase or of a partial peptide thereof in a sample of a biological fluid or of a tissue of a patient being determined and conclusions being drawn from the established presence and/or amount of the peptide determined with regard to the presence of an inflammation, of a severe infection or of a sepsis, and the result obtained being correlated with the severity of the sepsis and the possibilities for treatment and/or the prospects of treatment being estimated.

Instead of the determination of the epimerase or its fragments or optionally of posttranslationally modified forms thereof, the determination of the associated A1E-mRNA is also possible for diagnostic purposes. For diagnostic purposes, the epimerase determination can also be carried out indirectly as a determination of its enzyme activity in an inflamed organ or tissue or a biological fluid.

It is furthermore possible to carry out the determination of epimerase as a prognosis marker and marker for the monitoring of the course of inflammations, in particular systemic inflammations, and sepsis as part of a combination measurement with other markers.

In addition to combination with a procalcitonin measurement, combination of the measurement of epimerase with the determination of other markers for sepsis and systemic inflammations is particularly suitable, in particular with CA 19-9, CA 125, S100B, or S100A proteins involved in the regulation of inflammations, or with the determination of the novel sepsis markers inflammin (DE 101 19 804.3) and CHP (DE 101 31 922.3) described in the Applicant's prior, unpublished German Patent Applications mentioned below, with the determination of the enzyme glycine N-acyltransferase (GNAT) and/or with the determination of soluble cytokeratin fragments, in particular the newly discovered soluble cytokeratin-1 fragment (sCY1F; DE 101 30 985.6) and the known tumour marker CYFRA-21 or TPS and/or one or more of the above-mentioned prohormones. A simultaneous determination of the known inflammation parameter C-reactive protein (CRP) can also be envisaged. On the basis of the novel results described in this and the parallel Applications, a combination with measurements of known biomolecules or biomolecules still to be discovered, which are suitable as tissue- or organ-specific inflammation markers, should also be considered generally for fine sepsis diagnosis.

The content of said prior Applications of the Applicant is hereby incorporated by reference as part of the disclosure of the present Application.

Epimerase or its fragments or fusion products or the DNA coding therefor can also be used in preventive medicine or therapy. Thus, for example, suitable epimerase fragments can be used for the in vivo production of epimerase-binding antibodies by active immunization by techniques known per se. Those molecules which contain the complete epimerase or suitable partial sequences thereof in posttranslationally modified form, for example in glycosylated or phosphorylated form, or in a form substituted by pharmaceutical excipients, e.g. polyethylene glycol radicals, are also to be regarded as epimerase.

Epimerase or suitable partial sequences thereof may also serve as a target for therapeutic intervention in the sense that, by means of suitable specific binders for epimerase or partial peptides thereof, epimerase is deactivated intracorporeally or is optionally also eliminated extracorporeally from the circulation of patients in the sense of a "blood lavage", or plasmapheresis using suitable immunoadsorbents or using perfusable solid phases coated with specific binders for epimerase. As in other known cases in which a pathological process is influenced by modifying the effect and activity of enzymes involved therein, for example the known influencing of infectious diseases and colds by medicaments which are cyclooxygenase inhibitors, the action of A1E for therapeutic purposes can also be influenced with the aid of medicaments which have an enzyme-inhibiting, more precisely A1E-inhibiting, effect.

In addition to medicaments, in particular specific antibodies, especially humanized monoclonal antibodies, are suitable for the in vivo deactivation of epimerase. Therapeutic influencing of the inflammation cascade can, however, also be effected using the epimerase itself or epimerase agonists or antagonists. Such therapeutic interventions are possible particularly when further knowledge of the physiological function of the epimerase in an inflammatory process has been confirmed. It therefore appears that it cannot be ruled out at present that epimerase plays an important role in the inflammatory process, possibly by direct or indirect influencing of the pathological process by participation in (de)glycosylation steps and other metabolic processes in the activation or deactivation of peptides, proteins, lipids, sugar molecules and other substances.

The discovery and identification of the epimerase is described in more detail below, reference being made to the attached sequence listing. The figures show the following.

1. INFECTION SIMULATION BY ENDOTOXIN ADMINISTRATION IN AN ANIMAL MODEL (BABOONS)

On the basis of the experiments carried out with baboons for stimulating procalcitonin secretion by endotoxin injections (cf. H. Redl et al., "Procalcitonin release patterns in a baboon model of trauma and sepsis: Relationship to cytokines and neopterin", Crit Care Med 2000, Vol. 28, No. 11, 3659–3663; H. Redl et al., "Non-Human Primate Models of Sepsis", in: Sepsis 1998; 2:243–253), baboons (male, about 2 years old, 27 to 29 kg in weight) were each intravenously administered 100 µg of LPS (lipopolysaccharide from *Salmonella Typhimurium,* source: Sigma) per kg body weight. 5 to 5.5 h after the injection, the animals were sacrificed by intravenous administration of 10 ml of doletal. Within 60 min after their death, all organs/tissues were dissected and were stabilized by freezing in liquid nitrogen.

In the further processing, samples of individual frozen tissues (1 g) were mixed with 1.5 ml of buffer A (50 mM Tris/HCl, pH 7.1, 100 mM KCl, 20% glycerol) while cooling with nitrogen and were powdered in a porcelain mortar (cf. J. Klose, "Fractionated Extraction of Total Tissue Proteins from Mouse and Human for 2-D electrophoresis", in: Methods in Molecular Biology, Vol. 112: 2-D Proteome Analysis Protocols, Humana Press Inc., Totowa, N.J.). After subsequently centrifuging for 1 hour at 100,000 g and +4° C., the supernatant obtained was recovered and was stored at −80° C. until required for further processing.

Because experiments with the samples obtained as above showed that the largest amount of procalcitonin is found in liver tissue of treated animals, protein extracts from baboon liver were employed in the search for novel sepsis-specific biomarkers.

2. PROTEOME ANALYSIS USING CYTOPLASMIC LIVER CELL PROTEINS OF BABOONS

Cytoplasmic liver cell protein extracts of healthy baboons on the one hand (control) and, on the other hand, baboons which had been injected with LPS were used in a proteome analysis. In the initial analytical 2D gel electrophoresis, liver extract, containing 100 µg of protein, was standardized to 9 M urea, 70 mM DTT, 2% ampholyte pH 2–4 and then separated by means of analytical 2D gel electrophoresis, as described in J. Klose et al., "Two-dimensional electrophoresis of proteins: An updated protocol and implications for a functional analysis of the genome", Electrophoresis 1995, 16, 1034–1059. The visualization of the proteins in the 2D electrophoresis gel was effected by means of silver staining (cf. J. Heukeshoven et al., "Improved silver staining procedure for fast staining in Phast-System Development Unit. I. Staining of sodium dodecyl gels", Electrophoresis 1988, 9, 28–32).

Figure 1:
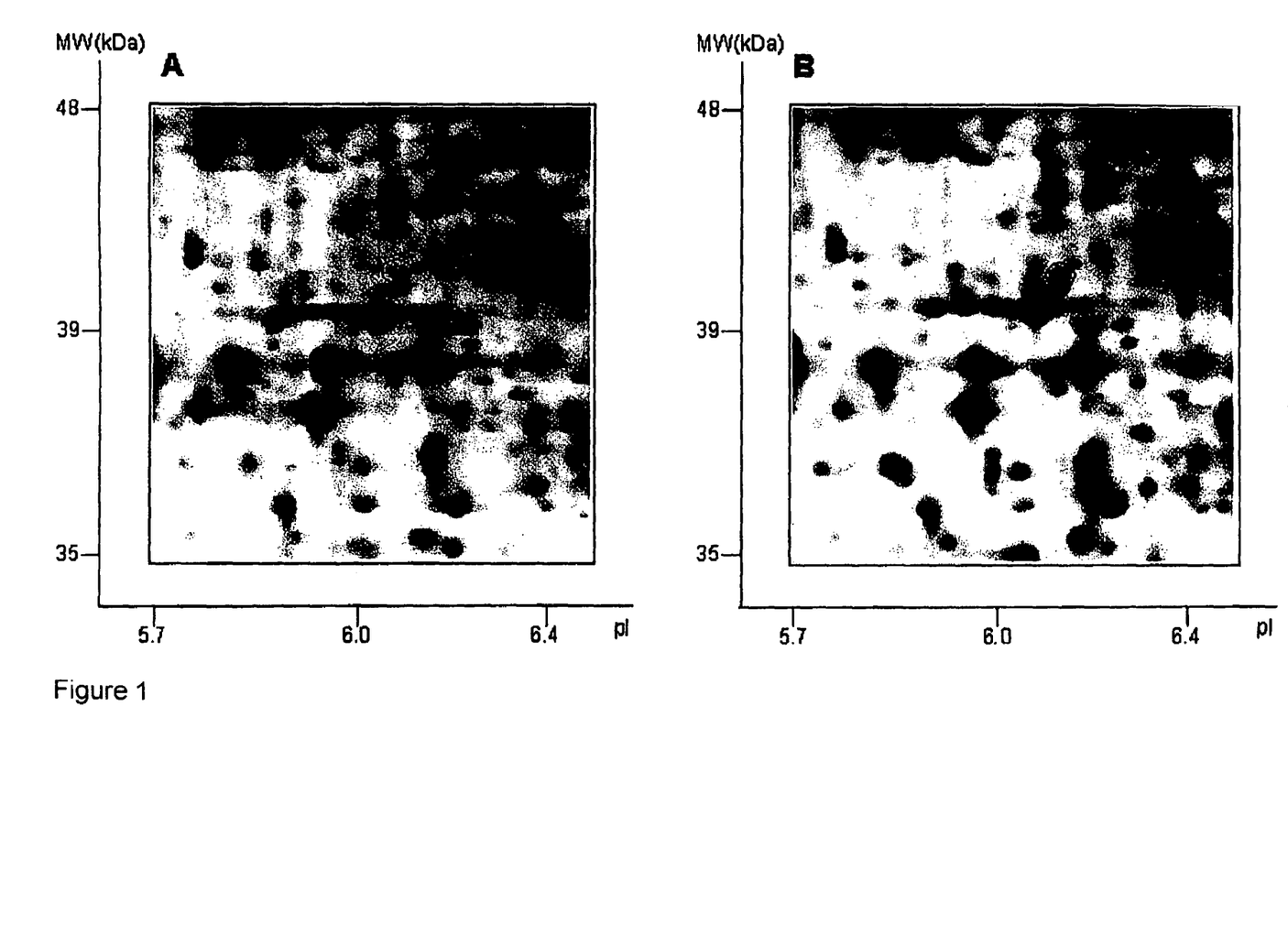
FIG. 1 shows views of 2D electrophoresis gels which permit a comparison of the spot patterns of cytoplasmic liver cell protein of a healthy baboon (A) with the liver cell proteins of a baboon 5 h after a sepsis induced by LPS administration (B). The arrow shows the position of the sepsis-specific product according to the invention, epimerase, which is singled out in diagram (B) by a circle.

For the evaluation, the protein spot patterns of the samples from untreated animals were compared with the protein spot patterns which resulted from liver tissue samples of treated animals. Substances which occurred in no control sample but additionally occurred in all treated animals were selected for further analytical investigations. FIG. 1 shows a comparison of the 2D electrophoresis gels for a control sample (A) and a sample from a treated animal (B), the additional protein spot in (B) corresponding to epimerase, the position of which is singled out by an arrow and a circle.

The novel specific proteins identified in the protein spot pattern of the analytical 2D gel electrophoresis were subsequently prepared by means of preparative 2D gel electrophoresis using 350 µg of protein (cf. once again (10)). In the preparative 2D gel electrophoresis, the staining was effected by means of Coomassie Brilliant Blue G250 (cf. V. Neuhoff et al., "Improved staining of proteins in polyacrylamide gels including isoelectric focusing gels with clear background at nanogram sensitivity using Coomassie Brilliant Blue G-250 and R-250", Electrophoresis 1988, 9, 255–262).

The protein spot preselected for the further analysis was cut out of the gel. It was trypsin-digested using the method which is described in A. Otto et al., "Identification of human myocardial proteins separated by two-dimensional electrophoresis using an effective sample preparation for mass spectrometry", Electrophoresis 1996, 17, 1643–1650, and then analyzed by mass spectroscopy, in particular using mass spectrometric investigations as described and discussed, for example, in G. Neubauer et al., "Mass spectrometry and EST-database searching allows characterization of the multi-protein spliceosome complex", in: nature genetics vol. 20, 1998, 46–50; J. Lingner et al., "Reverse Transcriptase Motifs in the Catalytic Subunit of Telomerase", in: Science, Vol. 276, 1997, 561–567; M. Mann et al., "Use of mass spectrometry-derived data to annotate nucleotide and protein sequence databases", in: TRENDS in Biochemical Sciences, Vol. 26, 1, 2001, 54–61. The trypsin-digested samples were subjected to tandem mass spectrometry after an ESI (ElectroSpray Ionization). A Q-TOF mass spectrometer having a so-called nanoflow-Z-spray ion source from Micromass, UK, was used. The working instructions of the apparatus manufacturer were followed.

3. IDENTIFICATION OF EPIMERASE

As shown in FIGS. 1(A) and 1(B), liver cell extracts of baboons to which an LPS injection had been administered contain, inter alia, a novel protein for which a molecular weight of about 40000±2000 Dalton was estimated on the basis of the gel electrophoresis data in comparison with marker substances having a known molecular weight, while an isoelectric point of about 6 to 6.4 was estimated from the relative position of the protein from the first dimension.

Figure 2:
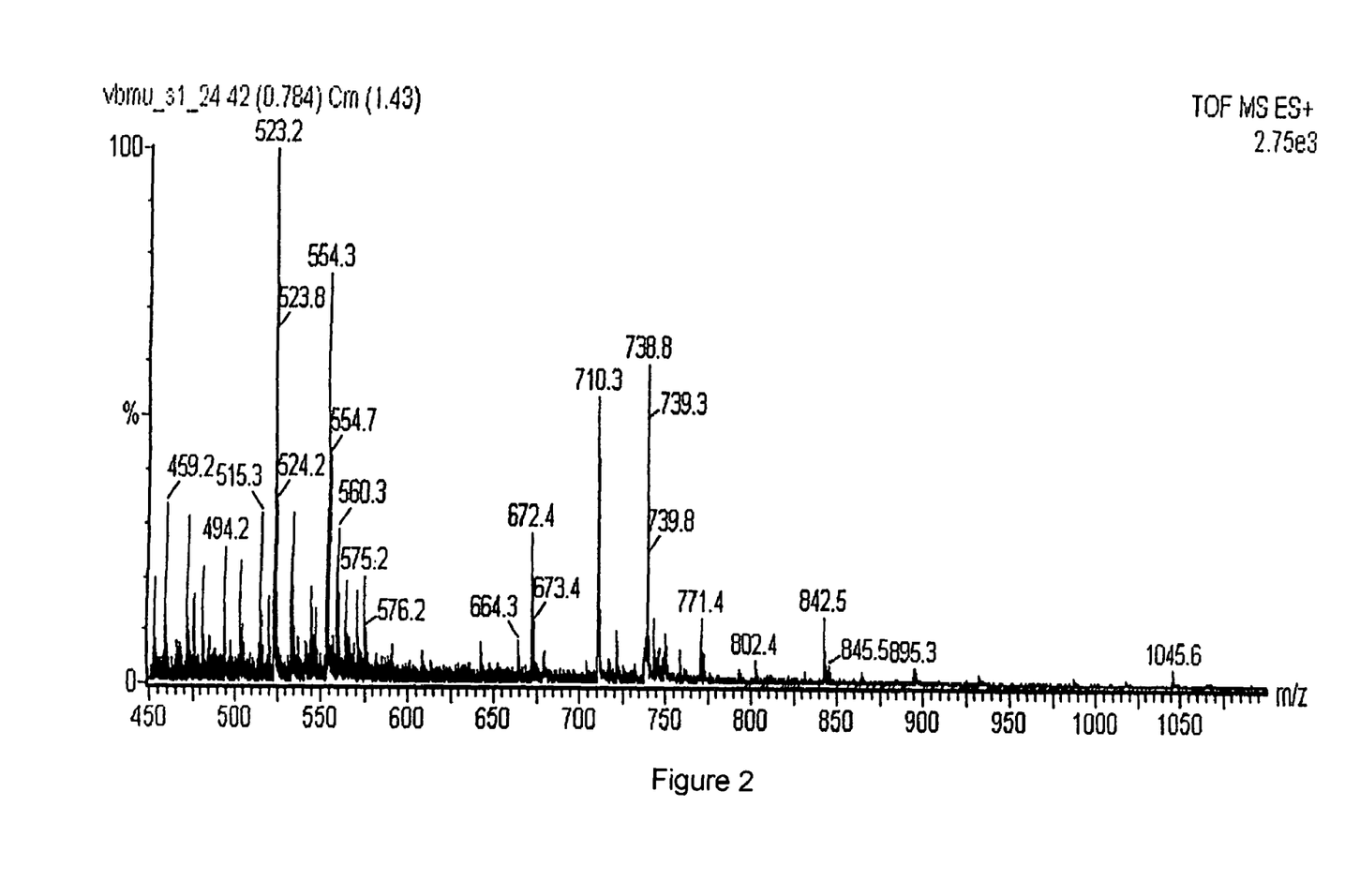
FIG. 2 shows the mass spectrum of the complete product A1E separated by 2D gel electrophoresis, isolated and then trypsin-digested.

This protein was analyzed by mass spectrometry, FIG. 2 showing the mass spectrum of the total trypsin-digested protein.

Figure 3:
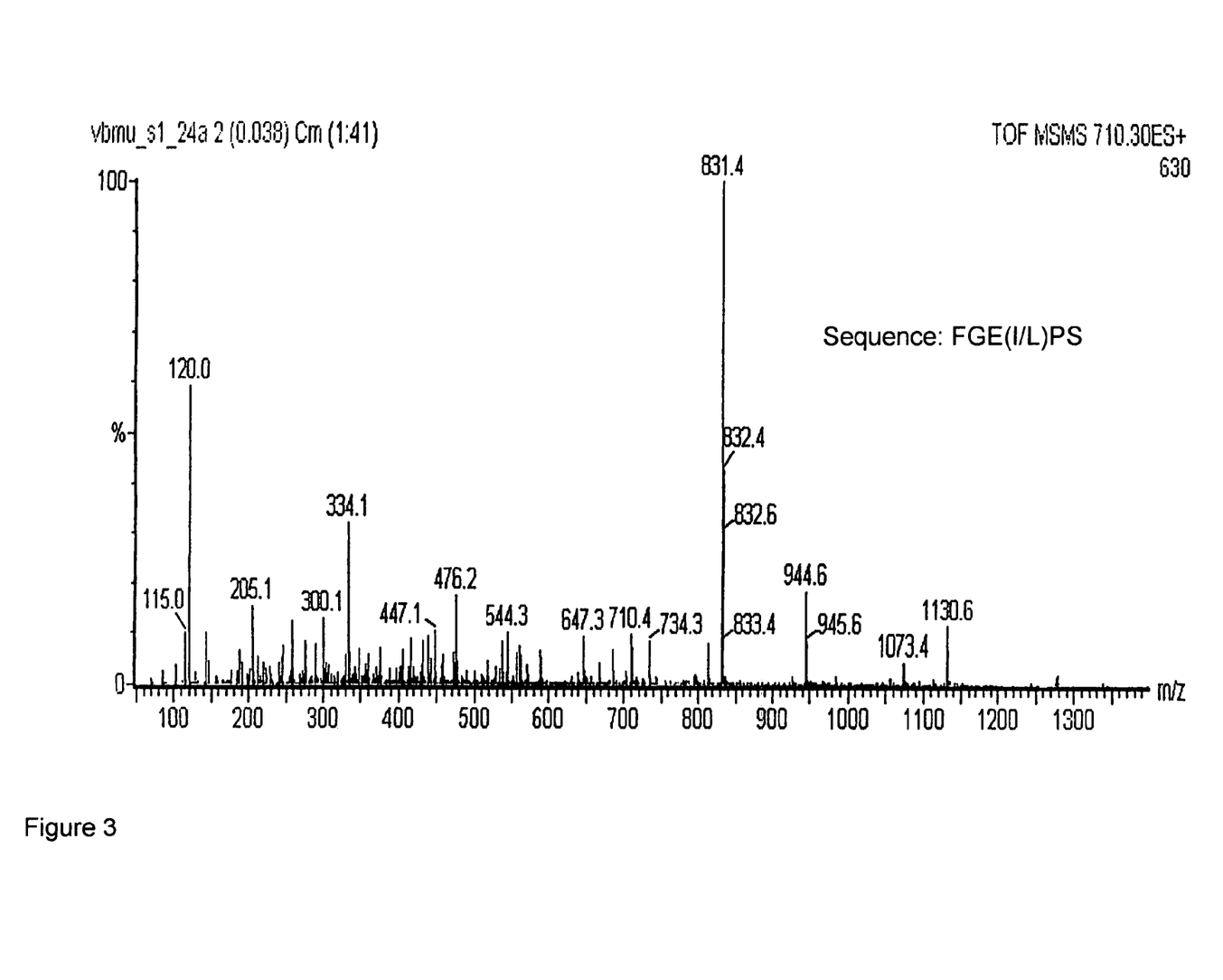
FIG. 3 shows the tandem mass spectrum of the A1E fragment 710.3 from FIG. 2, which has been subjected to an ESI-MS analysis.
Figure 4:
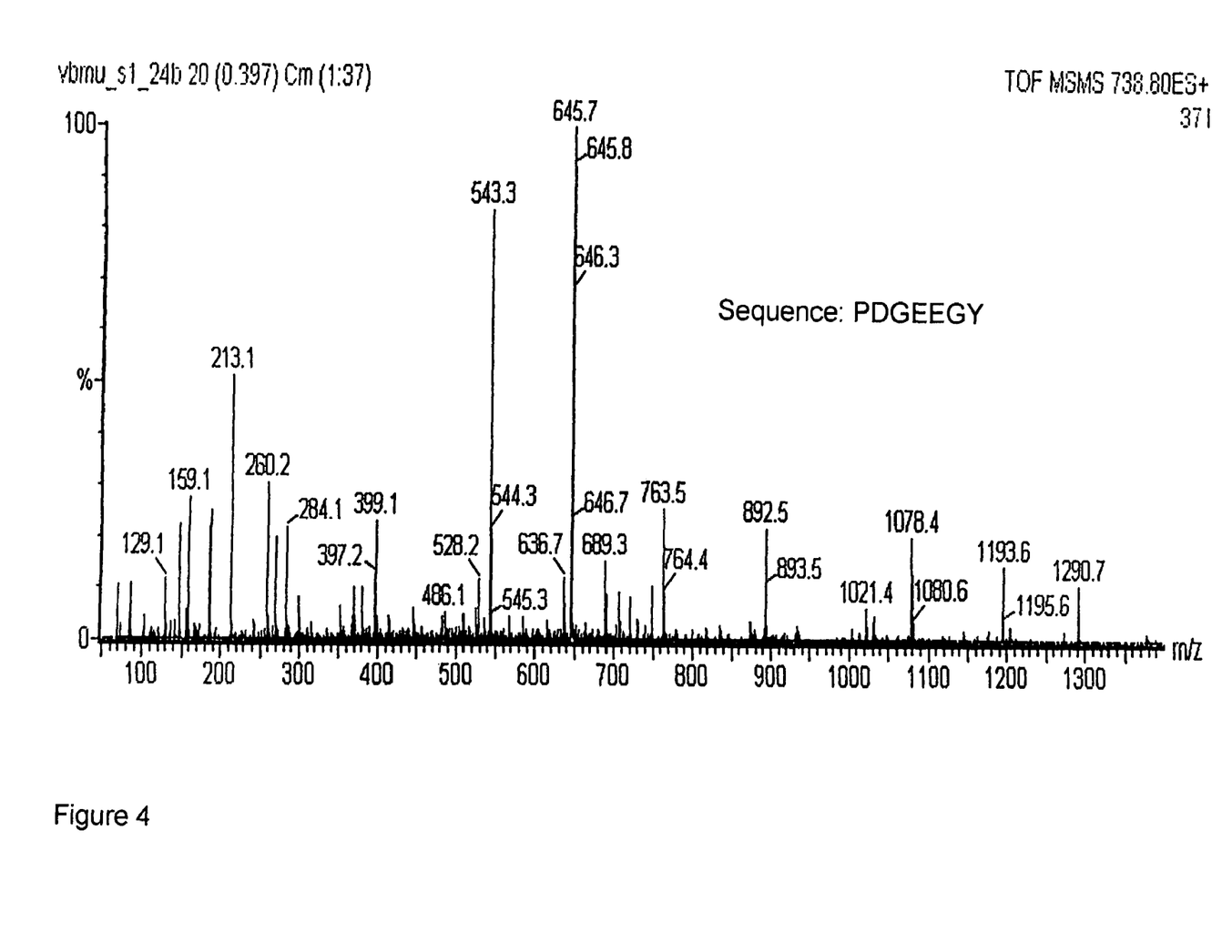
FIG. 4 shows the tandem mass spectrum of the A1E fragment 738.80 from FIG. 2, which has been subjected to an ESI-MS analysis.

Fragments of the "parent spectrum" according to FIG. 2 were identified by tandem mass spectroscopy. The mass spectra obtained for two of these fragments are shown in FIGS. 3 and 4. The fragments could be identified computationally in a manner known per se as the partial peptide sequences SEQ ID NO:1 and SEQ ID NO:2.

The partial sequences according to SEQ ID NO:1 and SEQ ID NO:2 identified by tandem mass spectrometry were then compared with the protein sequences which were available in sequence databases. An amino acid sequence for a hypothetical human protein comprising 342 amino acids with the theoretical molecular weight of 37765 Dalton (cf. SEQ ID NO:1), in which the partial sequences according to SEQ ID NO:1 and SEQ ID NO:2 were contained in the positions 9 to 14 and 134 to 140, respectively, was found in the cDNA database NCBI, Accession No. AAH14916. By sequence comparison with two amino acid sequences which are to be found using NiceProt View of TrEMBL and of which one is of human origin and comprises 204 amino acids (Entry name/Primary accession No. Q12915) and the other originates from pig kidneys (Entry name/Primary accession No. Q9GKX6), and both of which are assigned to aldose 1-epimerase, it was possible to identify the sequence according to SEQ ID NO:3 as an amino acid sequence of human aldose 1-epimerase.

The complete sequence of the human epimerase which is thus known explicitly makes it possible to prepare human epimerase or any partial sequences (fragments) thereof in a targeted manner for purposes of human medicine (diagnosis or therapy), and to do so using known synthetic or genetic engineering methods for the preparation of peptides. The same applies for purposes of veterinary medicine, it being possible in these cases to rely on corresponding known, e.g. bovine, epimerase sequences or it being possible easily to discover animal-specific epimerase sequences in corresponding animal-specific databases on the basis of the analogies with the known bovine and human sequences. Such peptides can then serve, for example in analogy to the procedure described in P. P. Ghillani et al., "Monoclonal antipeptide antibodies as tools to dissect closely related gene products", The Journal of Immunology, Vol. 141, No. 9, 1988, 3156–3163; and P. P. Ghillani et al., "Identification and Measurement of Calcitonin Precursors in Serum of Patients with Malignant Diseases", Cancer Research, Vol. 49, No. 23, 1989, 6845–6851, for providing suitable antibodies, in particular monoclonal antibodies, which in turn permit the provision of assays for the immunodiagnostic determination of epimerase or selected partial peptides thereof.

Monoclonal antibodies obtainable in the known manner described can also serve, particularly after humanization known per se, for the development of novel therapeutic agents (cf. the therapeutic approaches summarized in K. Garber, "Protein C may be sepsis solution", Nature Biotechnology, Vol. 18, 2000, 917–918). Furthermore, an in vivo neutralization of the epimerase is also possible by blocking the expression of the epimerase gene. The therapeutic interventions arising from the discoveries in the present Application also include administration of active substances which inhibit the enzyme activity of the epimerase.

It is furthermore within the scope of the present invention to use epimerase itself or partial peptides thereof as pharmaceutical active substances. The invention consequently also relates to pharmaceutical compositions which contain, as the actual active substance, one of the peptides according to the invention or antibodies produced against these peptides and prepared for administration to patients, together with a suitable pharmaceutical carrier.

The invention claimed is:

1. A method of differential early diagnosis and detection for the prognosis of, and therapy-accompanying assessment of the course of sepsis and severe infection in a patient in need thereof, the method comprising providing a biological fluid or a tissue sample from said patient, detecting and/or determining the presence and/or amount of human aldose 1-epimerase (A1E; SEQ ID #3) in the biological fluid or tissue sample from said patient, determining the presence, severity and course of the sepsis and severe infection, and evaluating the success of a therapy of the sepsis or severe infection in said patient.

2. The method according to claim 1, wherein the method is an immunodiagnostic assay.

3. The method according to claim 1, wherein the determination of human aldose 1-epimerase (A1E) is carried out indirectly as a determination of the associated A1E-mRNA or of the A1E enzyme activity.

4. The method according to claim 1, wherein at least one further sepsis parameter is simultaneously determined and a measured result in the form of a set of at least two measured quantities, which is evaluated for fine diagnosis of sepsis, is obtained as part of a multiparameter determination.

5. The method according to claim 4, wherein in the course of the multiparameter determination at least one further parameter is selected from the group consisting of procalcitonin, CA 19-9, CA 125, S100B, S100A proteins, soluble cytokeratin fragments, in particular CYFRA 21, TPS and/or soluble cytokeratin 1 fragments (sCY1F), the peptides inflaming and CHP, peptide prohormones, glycine N-acyltransferase (GNAT) and the C-reactive protein (CRP) is determined in addition to human aldose 1-epimerase.

6. The method according to claim 4, wherein the multiparameter determination is carried out as a simultaneous determination by means of a chip technology measuring apparatus or an immunochromatographic measuring apparatus.

7. The method according to claim 6, wherein the multiparameter determination obtained by means of the measuring apparatus is evaluated with the aid of a computer program.

8. The method according to claim 5, wherein the multiparameter determination is carried out as a simultaneous determination by means of a chip technology measuring apparatus or an immunochromatographic measuring apparatus.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Unknown Sequence
<220> FEATURE:
<223> OTHER INFORMATION: Description of Unknown Sequence: Unknown
      Primate (Pavian)

<400> SEQUENCE: 1

Phe Gly Glu Leu Pro Ser
 1               5

<210> SEQ ID NO 2
<211> LENGTH: 7
<212> TYPE: PRT
<213> ORGANISM: Unknown Sequence
<220> FEATURE:
<223> OTHER INFORMATION: Description of Unknown Sequence: Unknown
      Primate (Pavian)

<400> SEQUENCE: 2

Pro Asp Gly Glu Glu Gly Tyr
 1               5

<210> SEQ ID NO 3
<211> LENGTH: 342
<212> TYPE: PRT
<213> ORGANISM: Homo sapiens

<400> SEQUENCE: 3

Met Ala Ser Val Thr Arg Ala Val Phe Gly Glu Leu Pro Ser Gly Gly
 1               5                  10                  15

Gly Thr Val Glu Lys Phe Gln Leu Gln Ser Asp Leu Leu Arg Val Asp
                20                  25                  30

Ile Ile Ser Trp Gly Cys Thr Ile Thr Ala Leu Glu Val Lys Asp Arg
            35                  40                  45

Gln Gly Arg Ala Ser Asp Val Val Leu Gly Phe Ala Glu Leu Glu Gly
        50                  55                  60

Tyr Leu Gln Lys Gln Pro Tyr Phe Gly Ala Val Ile Gly Arg Val Ala
    65                  70                  75                  80

Asn Arg Ile Ala Lys Gly Thr Phe Lys Val Asp Gly Lys Glu Tyr His
                85                  90                  95

Leu Ala Ile Asn Lys Glu Pro Asn Ser Leu His Gly Gly Val Arg Gly
               100                 105                 110

Phe Asp Lys Val Leu Trp Thr Pro Arg Val Leu Ser Asn Gly Val Gln
           115                 120                 125
```

```
-continued

Phe Ser Arg Ile Ser Pro Asp Gly Glu Glu Gly Tyr Pro Gly Glu Leu
        130             135                 140

Lys Val Trp Val Thr Tyr Thr Leu Asp Gly Gly Glu Leu Ile Val Asn
145             150                 155                     160

Tyr Arg Ala Gln Ala Ser Gln Ala Thr Pro Val Asn Leu Thr Asn His
                165             170                     175

Ser Tyr Phe Asn Leu Ala Gly Gln Ala Ser Pro Asn Ile Asn Asp His
            180                 185                 190

Glu Val Thr Ile Glu Ala Asp Thr Tyr Leu Pro Val Asp Glu Thr Leu
        195             200                 205

Ile Pro Thr Gly Glu Val Ala Pro Val Gln Gly Thr Ala Phe Asp Leu
    210             215                 220

Arg Lys Pro Val Glu Leu Gly Lys His Leu Gln Asp Phe His Leu Asn
225             230                 235                     240

Gly Phe Asp His Asn Phe Cys Leu Lys Gly Ser Lys Glu Lys His Phe
                245             250                 255

Cys Ala Arg Val His His Ala Ala Ser Gly Arg Val Leu Glu Val Tyr
            260             265                 270

Thr Thr Gln Pro Gly Val Gln Phe Tyr Thr Gly Asn Phe Leu Asp Gly
        275             280                 285

Thr Leu Lys Gly Lys Asn Gly Ala Val Tyr Pro Lys His Ser Gly Phe
        290             295                 300

Cys Leu Glu Thr Gln Asn Trp Pro Asp Ala Val Asn Gln Pro Arg Phe
305             310                 315                     320

Pro Pro Val Leu Leu Arg Pro Gly Glu Glu Tyr Asp His Thr Thr Trp
                325             330                 335

Phe Lys Phe Ser Val Ala
                340
```